United States Patent
Grisel et al.

(10) Patent No.: US 10,114,007 B2
(45) Date of Patent: Oct. 30, 2018

(54) APPARATUS AND METHOD FOR ANALYZING BREATH GAS MIXTURE FOR HALITOSIS DETECTION

(71) Applicant: SUNSTAR SUISSE SA, Etoy (CH)

(72) Inventors: Alain Grisel, Lausanne (CH); Ulrike Lehmann, Lausanne (CH)

(73) Assignee: SUNSTAR SUISSE SA (CH)

(*) Notice: Subject to any disclaimer, the term of this patent is extended or adjusted under 35 U.S.C. 154(b) by 451 days.

(21) Appl. No.: 14/783,829

(22) PCT Filed: Apr. 4, 2014

(86) PCT No.: PCT/IB2014/000489
§ 371 (c)(1),
(2) Date: Oct. 9, 2015

(87) PCT Pub. No.: WO2014/167397
PCT Pub. Date: Oct. 16, 2014

(65) Prior Publication Data
US 2016/0054295 A1   Feb. 25, 2016

(30) Foreign Application Priority Data
Apr. 11, 2013 (CH) .................................. 0752/13

(51) Int. Cl.
*G01N 33/497* (2006.01)
*G01N 30/06* (2006.01)
(Continued)

(52) U.S. Cl.
CPC ......... *G01N 33/497* (2013.01); *G01N 1/2202* (2013.01); *G01N 30/06* (2013.01); *G01N 2030/8813* (2013.01)

(58) Field of Classification Search
CPC ........................... G01N 33/497; G01N 1/2202
(Continued)

(56) References Cited

U.S. PATENT DOCUMENTS

| | | | | |
|---|---|---|---|---|
| 5,205,845 A | * | 4/1993 | Sacks | G01N 1/26 73/23.41 |
| 5,322,626 A | * | 6/1994 | Frank | B01D 11/0203 203/49 |

(Continued)

OTHER PUBLICATIONS

Tangerman, A and Winkel E G. "The Portable gas chromatograph OralChroma (TM): a method of choice to detect oral and extra-oral halitosis". Mar. 2008. Journal of Breath Research. vol. 2.*

(Continued)

*Primary Examiner* — Son Le
*Assistant Examiner* — Tarun Sinha
(74) *Attorney, Agent, or Firm* — Galbreath Law Offices, P.C.; John A. Galbreath

(57) ABSTRACT

An apparatus for detecting and separating specific compounds in breath gas mixtures for halitosis analysis consisting of a line (1) for delivering a pressure-controlled neutral gas; a removable connected sample chamber (2) of specific volume for receiving the gas mixture to be evaluated; an electronically controlled valve (8) for injecting the gas sample into the line (1); a temperature-controlled microfabricated separation capillary column (4) arranged to receive the gas sample injected into the line (1); a gas sensor (5) at the outlet of the capillary column (4) and a control interface (6) for managing the measurement and evaluating the obtained data.

16 Claims, 1 Drawing Sheet

(51) Int. Cl.
   *G01N 1/22*      (2006.01)
   *G01N 30/88*     (2006.01)

(58) Field of Classification Search
   USPC .......................................................... 73/23.3
   See application file for complete search history.

(56)  References Cited

U.S. PATENT DOCUMENTS 5,588,988 A     12/1996  Gerstel
   6,625,975 B1 *   9/2003  Stahl .................. B01D 53/9431
                                                   60/286
   7,735,352 B2 *   6/2010  Alm ..................... G01N 30/463
                                                   73/23.4
   2008/0103338 A1 * 5/2008 Ladebeck .............. B01J 23/868
                                                   568/814
   2011/0127421 A1 * 6/2011 Finlay ................... G01N 30/72
                                                   250/283
   2013/0174642 A1 * 7/2013 Bourlon ................ B01J 20/103
                                                   73/23.39

OTHER PUBLICATIONS

Tangerman et al.: "The portable gas chromatograph OralChroma (TM): a method of choice to detect oral and extra-oral halitosis", Journal of Breath Research IOP Publishing Ltd. UK, vol. 2, No. 1, Mar. 2008 (Mar. 2008), XP002726883, ISSN: 1752-7163.

* cited by examiner

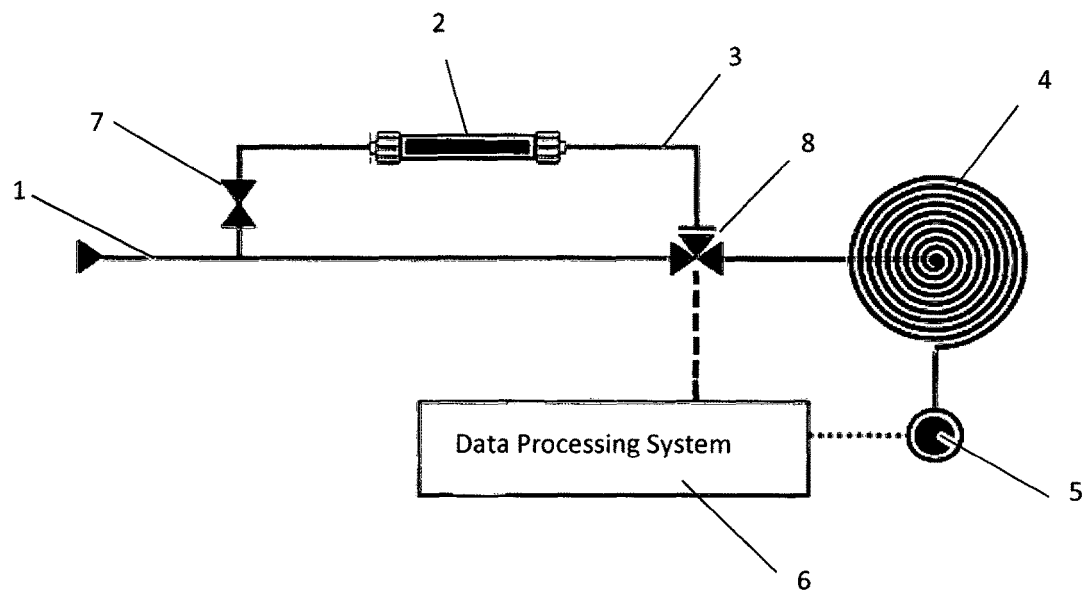

APPARATUS AND METHOD FOR ANALYZING BREATH GAS MIXTURE FOR HALITOSIS DETECTION

The present invention relates to an apparatus and a method for analyzing a gas mixture for breath gas qualification, and more specifically for halitosis detection.

Alveolar and intraoral breath is a distinctive gas whose chemical composition differs markedly from inspired air. Some gaseous compounds are either subtracted from inspired air (by degradation and/or adsorption in the body) or added to exhaled air (breath) as products of metabolism. Some features of this transformation have been well understood for many years: e.g. oxygen is subtracted and carbon dioxide is added by the oxidative metabolism of glucose (Phillips M., Breath tests in medicine, Scientific American 1992:267(1):74-79). Pauling et al, in 1971, employed cold trapping to concentrate volatile organic compounds (VOCs) in breath and found that normal human breath contained several hundred different VOCs in low concentrations (Pauling L. Robinson AB, Teranishi R and Cary P: Quantitative analysis of urine vapor and breath by gas-liquid partition chromatography, Proc Nat Acad Sci USA 1971:68:2374-6). This observation has been subsequently confirmed in many different laboratories, progressively employing more sophisticated and sensitive assays. More than a thousand different VOCs have been observed in low concentrations in normal human breath (Phillips M: Method for the collection and assay of volatile organic compounds in breath, Analytical Biochemistry 1997; 247:272-278).

Breath gas analysis is a method for gaining non-invasive information on the clinical state of an individual by monitoring volatile organic compounds present in the exhaled breath. Hereby, breath gas composition can be related to the concentration of certain compounds in blood via mathematical modeling as for example in blood alcohol testing. Other applications include asthma detection by exhaled nitric oxide, lung cancer detection, diabetes detection, fructose mal-absorption with hydrogen breath test, helicobacter pylori with urea breath test, or diagnosis of organ rejection.

The most common application is the detection of halitosis related to sulphur compounds in the breath mainly due to bacterial infection in the oral cavities. Breath analysis can be done with various measurement methods such as gas chromatography using mass spectrometry as detection unit, but there are also simpler methods for specific purposes, such as the Halimeter (Interscan) and the breathalyzer (for example: Dräger Alcotest 3000 from Dräger).

The traditional organoleptic method for diagnosis of oral halitosis is based on smelling the exhaled air of mouth and nose separately and comparing the two. This method is widely used but not accurate. A halimeter detects volatile sulphide compounds with a simple appropriate sensing device without specifically separating the gaseous breath compounds. It is used in the assessment of bad breath as a complement to the traditional organoleptic measurement. Finally, systems based on gas chromatography have been developed (e.g. OralChroma), which separate and measure molecular levels of the three major volatile sulphur compounds in a sample of exhaled air (hydrogen sulphide, methyl mercaptan and dimethyl sulphide).

Gas chromatography is a well-established analytical technique that is commonly used for the separation and detection of the various chemical components present in gases and low boiling point liquids. The technique is widely used in organic chemistry research, pharmaceutical development, and forensic specimen analysis. A gas chromatography system typically has five major components: a carrier gas; a sample injector; a gas chromatography column; a detector; and a data processing system. The carrier gas, also referred to as the mobile phase, is a highly-pure and relatively inert gas, such as helium. The carrier gas flows through the column throughout the separation process. The sample injector introduces a precise and, typically, very small volume of the sample, in gaseous form, into the carrier gas flowing through the column. The gaseous sample typically includes a number of different chemical components that are intended to be separated by the gas chromatograph. To effect this separation, the inside of the column is coated with a stationary phase that adsorbs the different chemical components in the sample to differing degrees. These differences in adsorption cause differing propagation delays for the chemical components as they travel down the column, thereby effecting a physical separation of the sample into its chemical components. The detector is located after the column and serves to detect the various chemical components in the sample as they emerge from the column at different times. The data processing system reads the detector and is typically able to store, process, and record the results.

The aim of the present invention is to propose an apparatus for analyzing exhaled breath for fast halitosis diagnosis. Therefore the invention is devoted to the detection and identification of volatile sulphur compounds with a controlled short measurement time and clear separation.

According to the invention, an apparatus for separating specific chemical compounds such as volatile sulphur compounds (VSC) in a gas mixture, comprises a line for delivering pressure controlled carrier gas, an exchangeable chamber for breath sample collection, an automatic system for the breath sample injection and a separation capillary column allowing the gaseous compounds to be selectively detected at the capillary outlet using a semiconductor gas sensor.

The invention aims at providing a portable gas analysis system based on the principle of gas chromatography but comprising of modules tailored towards the rapid and specific detection of compounds characteristic for halitosis. The gas sample is collected in an exchangeable sample chamber of a specific volume that can be inserted into and removed from a bypass of the line for delivering a carrier gas at a controlled constant pressure set typically between 0.15 and 0.5 bar. The exchangeable sample chamber may optionally function as a pre-concentrator element where the specific compounds of the gas sample can be trapped at room temperature and released by heating the pre-concentrator walls. The working principle consists of injecting the equally pressurized gas sample to be analyzed from the sample chamber into the continuous stream of the carrier gas such as pressurized ambient air, by way of electronically controlled valves. The sample is transported by the carrier gas through a temperature controlled micro-fabricated separation column that separates the gas compounds of interest over time. The pressure of the carrier gas, the length of the capillary column, its temperature and inner wall coating are chosen with respect to achieving a sufficient separation of the compounds of interest in the shortest possible time for the sample analysis. The gaseous compounds are detected at the capillary column outlet using a non-selective but highly sensitive micro-gas sensor with a fast response and recovery time. The compounds are then identified by automatic peak detection, the concentration being evaluated according to a specific calibration using reference gases.

The invention will be more clearly understood from the following description of a preferred embodiment, which is given by way of example only, with reference to the accompanying schematic drawing, in which:

FIG. 1 is a diagram of an apparatus according to the invention.

In a preferred embodiment, the illustrated diagram (FIG. 1) of an apparatus according to the present invention comprises a carrier gas line (1); an exchangeable sample chamber (2); a sample injection line (3); a micro fabricated separation column with polymer coating of the inner walls (4); a gas detector (5); and a data processing system (6).

The carrier gas line (1) supplies synthetic or ambient air at constant pressure into the system. The pressure in line (1) as well as the connected sample chamber (2) is typically between 0.15 to 0.5 bar, and is chosen thus, that the detection time of the specific compound to be measured falls well into the limits of the measured time. The pressure can be generated by a pump or the carrier gas container.

The gas mixture to be analyzed (notably samples of exhaled breath containing sulphur compounds) is filled into a fixed volume chamber (2) which can be exchanged between two measurements after closing the 2 way valve (7). The chamber (2) is in the simplest case a tube with a cap at each end. For sample collection, a test subject breathes directly into the tube (2), closes the tube for transport by fitting the caps. Subsequently, the tube (2) can be installed in the apparatus, as shown in FIG. 1. After installing the sample chamber, the inlet valve (7) is opened to pressurize the sample volume.

The injection of the sample by line (3) into the carrier gas line (1) stream and subsequently into the capillary column (4) is electronically controlled by the 3 way valve (8) which lets the sample (3) pass for a preset injection time. Typically, the injection time is chosen between 0.5 s and 3 s. The start of the injection time sets the beginning of the measurement time.

In a preferred embodiment, the capillary column (4) is a micro-fabricated channel of a high length to cross-section ratio. The capillary column (4) is internally coated with a polymer such as PDMS (Polydimethylsiloxane). The capillary column's (4) length, width and height are designed with respect to the specific gaseous compounds to be separated and detected within the chosen measuring time. Typically, the length is chosen between 1 to 5 m, the width between 30 to 150 µm (micron) and the height between 50 to 250 µm (micron).

The gaseous compounds are detected at the capillary (4) outlet using a non-selective but highly sensitive micro-gas sensor (5) with a fast response and recovery time. The non-selectivity and high sensitivity of the gas sensor is discussed as follows:

Non-selective: The semiconductor gas sensor used in the apparatus is non-selective, meaning that it is sensitive to all oxidizing or reducing gases. In particular, the gas sensor will detect most of VOC (Volatile Organic Compounds) of interest (i.e: VSC). The sensor itself is not able to distinguish compounds in a mix of VOC, which is why a pre-treatment (filter, separation via micro-column) is required. If the selectivity is obtained via the column which separates the different gas molecules, the gas semiconductor gas sensor will detect the different gaseous compounds through time separation.

Highly sensitive: The semiconductor gas sensor is highly sensitive to the VOC of interest meaning it can detect the isolated/separated gaseous compounds in the ppb-ppm range.

There are various detectors (5) which can be used for the detection of volatile organic compounds. The gas sensor (5) may be a semiconductor gas sensor micro-fabricated in silicon. The sensor (5) is, as shown, positioned directly at the output of the capillary column (4). The sensor signal is recorded by the data control system (6), allowing to identify and quantify the compounds by automatic peak detection, the concentration being evaluated according to a specific calibration using reference gases combined with peak area comparative calculation.

The overall measurement is controlled by the data processing system (6) which comprises a micro-controller for automatic control of the measurement sequence such as the sample injection, the injection and measurement time.

The preferred embodiment of the inventive apparatus is dedicated to breath gas analysis, for halitosis diagnostics. The elements of the apparatus are tailored to detect specific compounds in breath such as H2S (hydrogen sulphide), CH2SH (methyl mercaptan), (CH3)2S (dimethyl sulphide), known to be markers for halitosis.

The invention claimed is:

1. An apparatus for separating specific compounds in a gas mixture, the apparatus comprising: a line for delivering a pressure-controlled neutral carrier gas, said line including a bypass for the pressure-controlled neutral gas; a sample chamber of specific volume for collecting a gas mixture to be examined, the sample chamber being removably connectable in the bypass of to the line in a bypass configuration relative to the line for pressurizing the gas sample before injection of the sample into the line; means configured to inject the pressurized gas sample from the bypass into said line during a pre-set injection time when the sample chamber is connected to in the bypass of said line and has been pressurized by said pressure-controlled carrier gas; a temperature-controlled separation capillary column arranged to receive the gas sample injected into said line; a gas sensor at the outlet of the capillary column; and a data processing system configured to automatically control the measurement sequence including the sample injection, the injection time and the measurement time.

2. An apparatus according to claim 1, wherein the exchangeable sample chamber is a pre-concentrator element.

3. An apparatus according to claim 1, wherein the gas sensor is non-selective but highly sensitive.

4. An apparatus according to claim 1, wherein the sample chamber is removably connectable in said bypass to said line by means of two valves.

5. An apparatus according to claim 1, wherein said data processing system is further configured for compound recognition by automatic peak detection and relative concentration by peak area comparative calculation.

6. An apparatus according to claim 1, wherein the capillary column's length is comprised between 1 to 5 meters, the capillary column's height is comprised between 50 to 250 micrometer, the capillary column's width is comprised between 30 to 150 micrometer.

7. An apparatus according to claim 1, wherein the said capillary column is unfilled but internally coated with a polymer.

8. An apparatus according to claim 7, wherein the polymer is polydimethylsiloxane.

9. An apparatus according to claim 1, comprising a miniature pumping system for generating said neutral carrier gas from ambient air.

10. An apparatus according to claim 1, for halitosis diagnosis.

11. A method for separating specific compounds in a gas mixture, the method comprising: delivering a pressure-controlled neutral carrier gas via a line which includes a bypass for the pressure-controlled neutral carrier gas; collecting a gas mixture to be analyzed in a sample chamber of specific volume, the sample chamber being removably connectable in the bypass of said line in a bypass configuration relative to the line; connecting the sample chamber to the bypass of said line for pressurizing the sample volume in the bypass by pressure-controlled carrier gas from the line; injecting the pressurized gas sample from the bypass into said line during an injection time chosen between 0.5 and 3 seconds; receiving the gas sample injected into said line in a temperature-controlled separation capillary column; and sensing the separated gas compounds at the outlet of the capillary column via a highly sensitive but non-selective gas sensor.

12. A method according to claim 11, wherein the injection of the gas sample into the line takes place in a pressure range between 0.15 to 0.5 bar.

13. A method according to claim 11, comprising generating said neutral carrier gas from ambient air using a miniature pumping system.

14. A method according to claim 11, wherein compound recognition is performed by automatic peak detection and relative concentration is determined by peak area comparative calculation using a data processing control system.

15. A method according to claim 1, for halitosis analysis.

16. A method according to claim 15, wherein the specific compounds detected in breath are H2S (hydrogen sulphide) and/or CH2SH (methyl mercaptan) and/or (CH3)2S (dimethyl sulphide).

* * * * *